United States Patent [19]

D'Antonio

[11] Patent Number: 4,859,464

[45] Date of Patent: Aug. 22, 1989

[54] METHOD FOR THE PURIFICATION OF PARASITE ANTIGENIC FACTORS

[76] Inventor: Lawrence E. D'Antonio, 1000 Clifton Ave., Collingdale, Pa. 19023

[21] Appl. No.: 600,596

[22] Filed: Apr. 16, 1984

Related U.S. Application Data

[63] Continuation of Ser. No. 349,616, Feb. 17, 1982, abandoned.

[51] Int. Cl.$^4$ ..................... C12P 21/00; A61K 39/00; A61K 37/00
[52] U.S. Cl. ........................................ 424/88; 435/68; 435/70; 514/2; 514/8; 530/350; 530/359; 530/395; 530/402; 530/822; 530/419; 530/421; 530/422; 530/423; 530/426
[58] Field of Search .......................... 424/85, 88, 92; 260/112 B, 112 R; 514/2, 6, 12, 8; 530/359, 418, 420, 421, 422–426, 822, 350, 395, 402, 412, 419, 829; 435/68, 70

[56] References Cited

FOREIGN PATENT DOCUMENTS

| | | | |
|---|---|---|---|
| 0003529 | 8/1979 | European Pat. Off. | 424/88 |
| 8302896 | 9/1983 | PCT Int'l Appl. | 421/88 |
| 2096893 | 10/1982 | United Kingdom | 424/88 |
| 2099300 | 12/1982 | United Kingdom | 424/88 |

OTHER PUBLICATIONS

Grothhaus et al *Infec and Immun* Apr. 1980, vol. 28(1) pp. 245–233 "Isolation of a Souble Component of *Plasmodium berghei* which induces immunity in rats".

Kilejian *Proc. Natl Acad Sci* vol. 77(6) Jun. 1980 pp. 3695–3699 "Stage-specific proteins and glycoproteins of *Plasmodium Falciparum:* Identification of antigens unique to schizonts and merozoites".

D'Antonio et al *Science* vol. 168 pp. 1117–1118 1970.

D'Antonio et al *Exptl Parasitology* vol 31 pp. 75–81 1972.

D'Antonio et al *Immunolgy Serolog Aspects of Clin Parasitology* p. 59 1981.

Miller *Biochem Biophys Res Comm* vol. 40 (3) 1970 "Total Solubilization of erythrocyte membranes by non-ionic detergents".

Ludford et al *Exp Parasit* vol. 32 pp. 317–326 1972.

Cox et al *Amer J Trop Med Hygiene* vol. 17 (2) 1968 pp. 173–179.

Primary Examiner—Thomas G. Wiseman
Assistant Examiner—Robin Lyn Teskin
Attorney, Agent, or Firm—D. Peter Hochberg; Mark M. Kusner; Walter C. Danison, Jr.

[57] ABSTRACT

A method for the solubilization and recovery of insoluble parasite protective antigenic factors associated with parasite material comprising solubilizing the antigenic factors with a non-ionic detergent and separating the solubilized material from undispersed residual material. The purified protective antigenic factors are useful as vaccines, particularly against malaria, and as diagnostic agents.

15 Claims, 3 Drawing Sheets ered according to the invention to a mammal or other vertebrate in immunityconferring doses. The invention particularly provides a method for the direct extraction of parasite antigenic factors from intact erythrocytes infected with malarial parasites of the genus Plasmodium, particularly *P. berghei, P. malariae, P. vivax, P. knowlesi, P. ovale,* and *P. falciparum,* and a method for immunizing mammals or other vertebrates against infection by these parasites. Also, the invention provides a method for diagnosing infection by protozoan parasites.

METHOD FOR THE PURIFICATION OF PARASITE ANTIGENIC FACTORS

This is a continuation of co-pending application Ser. No. 349,616 filed 2/17/82, abandoned.

BACKGROUND OF THE INVENTION

The need for vaccines to control malaria and other parasitic diseases remains unabated. For malaria, the need is particularly pressing as it continues to dominate vast subtropical and tropical areas of the world. An effective vaccine against this disease would contribute significantly to restraining it and dulling the sharp cutting edge of its repeated resurgence.

For lack of effective immunization procedures, malaria and other parasitic diseases continue for the most part to be treated after inception, with varying degrees of success. While numerous attempts have been made to isolate protective antigenic factors associated with these parasites, purification and recovery of antigens having a high immunizing efficiency in quantities suitable for large scale administration have not been effected for most infectious parasitic diseases.

Rodents and primates have been variously vaccinated against malaria with crude plasmodial fragments separated from host blood cells {see e.g., D'Antonio, et al., *Nature* 223: 507–509 (1969) (Reference I); D'Antonio, et al., *Science* 168: 1117–1118 (1970) (Reference II); D'Antonio, et al., *Exptl. Parasitology* 31: 75–81 (1972) (Reference III)}, isolated membrane particles {see e.g., References II; III; D'Antonio, et al., *J. Am. Osteopathic Assoc.* 73: 649–652 (1974) (Reference IV); Speer, et al., *J. Protozool.* 23: 437–442 (1976) (Reference V)}, and most recently, purified membrane subfractions {see e.g., D'Antonio, et al. in *Immunological and Serological Aspects of Clinical Parasitology,* W. Ball and V. Iralou, Eds. (Eastern Penn. Branch of the Am. Soc. for Microbiology, P. 59, 1981) (Reference VI}. However, further purification of the involved protective antigen(s) has been hampered by the absence of effective non-denaturing techniques for separating them from their insoluble carrier components. For example, specific attempts to isolate malarial plasmodial protective antigens from associated plasmodial material with acetic acid (D'Antonio, et al., *Abs. of the Am. Soc. for Microbiol.,* Abstr. E68, 1980) or lithium 3,5-diiodosalicylate (Reference VI and D'Antonio, et al., *Abs. of the Am. Soc. for Microbiol.,* Abstr. E98, 1979) have not proved entirely successful. Thus, solubilization and recovery of such antigenic factors from these and related materials would open the way for their final purification and is the next crucial step in advancing the immunochemistry, immunobiology, and vaccine technology of malaria and related diseases.

SUMMARY OF THE INVENTION

Accordingly, the invention comprises a method for the solubilization and recovery of protective antigenic factors associated with protozoan parasites. The invention further comprises a method for the purification and recovery of protective antigens of protozoan parasites, particularly parasites of the genuses Plasmodium, Babesia, Trypanosoma, Leishmania, Trichomonas, Entamoeba, Toxoplasma, Pneumocystis, Aegyptianella, Theileria, Anaplasma, and most particularly intraerythrocytic protozoan parasites. The invention additionally provides a vaccine capable of conferring immunity against such parasites comprising the antigenic factors purified and recovered according to the invention. The invention further includes a method for conferring immunity against protozoan parasites comprising administering the parasite antigenic factors purified and recovered according to the invention to a mammal or other vertebrate in immunityconferring doses. The invention particularly provides a method for the direct extraction of parasite antigenic factors from intact erythrocytes infected with malarial parasites of the genus Plasmodium, particularly *P. berghei, P. malariae, P. vivax, P. knowlesi, P. ovale,* and *P. falciparum,* and a method for immunizing mammals or other vertebrates against infection by these parasites. Also, the invention provides a method for diagnosing infection by protozoan parasites.

Broadly, the invention comprises a method for the solublization and recovery of parasite protective antigenic factors associated with parasite material comprising dispersing the antigenic factors from intact or fractured cells or other tissues infected with protozoan parasites or from free parasite forms with a non-ionic detergent, and separating the solubilized antigenic factors from the dispersing agent and cell or tissue residues. The recovered antigenic factors are useful in vaccines for conferring specific immunity in mammals or other vertebrates to the infecting parasite, or as diagnostic agents.

DETAILED DESCRIPTION OF THE INVENTION

By the process of the invention, insoluble parasite antigenic factors associated with insoluble parasite components, particularly the parasite membrane, are recoverable in large quantities from parasite starting material comprising infected intact cells or tissues, partially purified parasite membrane material, or free forms of the parasite.

The methods and compositions of the invention are applicable to blood and tissue infecting parasites such as parasites of the genuses Plasmodium, Babesia, Theileria, Aegyptianella, Anaplasma, Trypanosoma, Leishmania, Trichomonas, Entamoeba, Toxoplasma, Pneumocystis, and particularly the Plasmodium species causing malaria such as *P. malariae, P. vivax, P. ovale, P. falciparu, P. berghei, P. knowlesi,* and similar intraerythrocytic and tissue protozoan parasite species of the Babesiidae and Trypanosomatidae families.

The protective antigenic factors associated with these parasites are recoverable by the process of the present invention from free forms of the parasites in various stages of development, from parasite infected tissues such as liver or skin tissues, or from infected blood, lymph or other body fluids, particularly red blood cells. For example, plasmodial antigenic factors are recoverable from the sporozoite stage of the parasite by either separating the sporozoites from the host mosquito or isolating them from another environment, or by processing the entire mosquito or culture mixture containing the sporozoites according to the process of the present invention. Plasmodial antigenic factors are also recoverable in purified form from other forms of the parasite such as gametes, microgametes, ookinetes, merzoites, and ring or segmenter forms, as well as from infected liver or blood tissue, particularly erythrocytes. The infected tissues or cells may be pretreated to partially purify the parasitic material in association with the antigenic factors, or intact cells or tissues may be employed in the process of the invention. Accordingly, the starting parasite material useful in the process of the present invention comprises both homogeneous and heterogenous preparations of different stages or forms of the parasite, either in the absence or presence of unrelated cells or other substances found in typical in vitro cultures or in in vivo host tissues.

According to the invention, insoluble protective antigenic factors of these parasites are directly solubilized and recovered from the starting parasite material by solubilizing the protective antigenic factors with a dispersing agent comprising a non-ionic detergent, and separating the solubilized antigenic factors from the insoluble residual material and detergent. The recovered purified antigenic material has enhanced immunoprotective activity owing to both the high concentration of antigenic factors in the recovered material, and, it is believed, the removal of immunosuppressive substances produced by the parasite.

Figure 1:
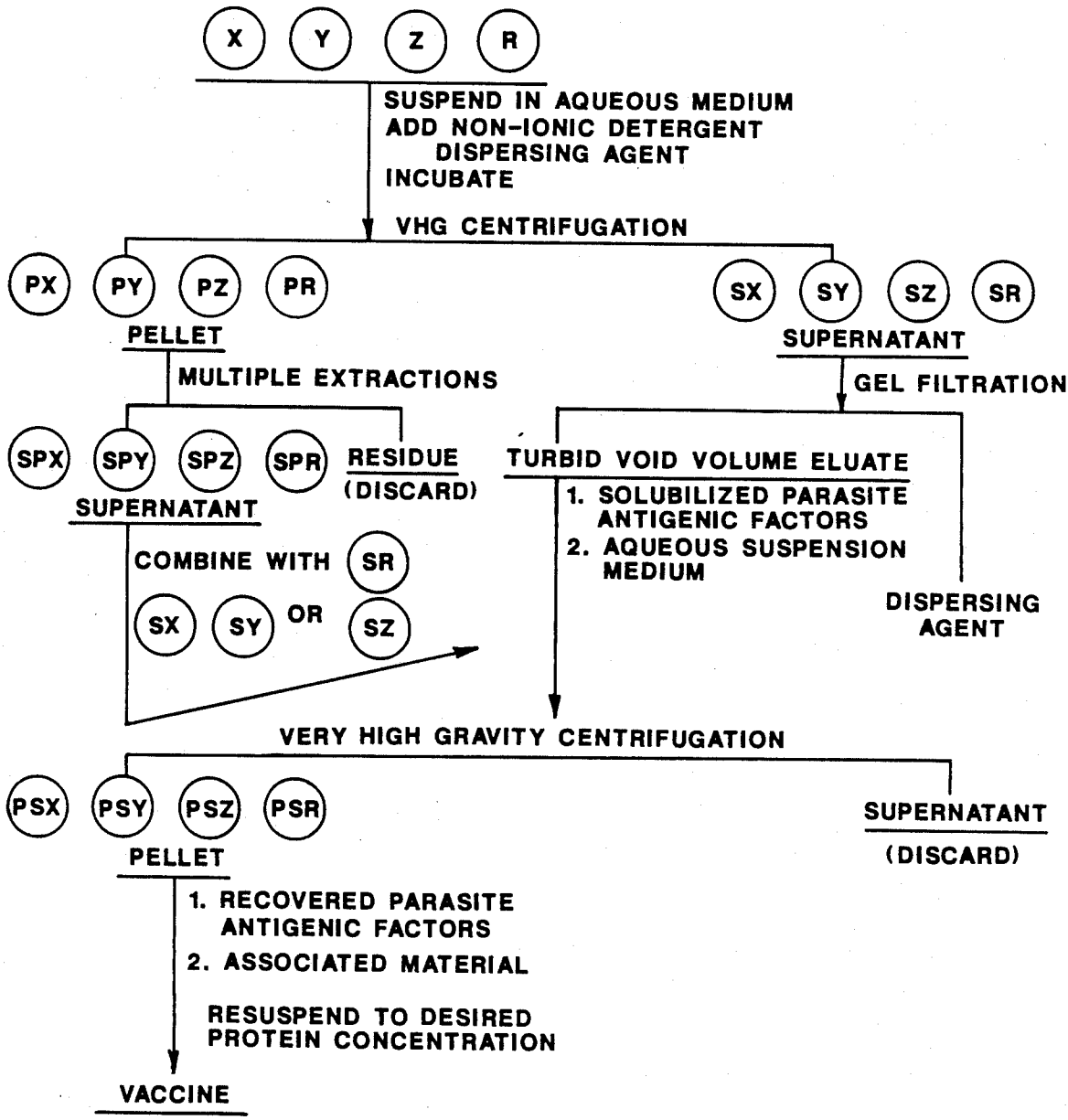
FIG. 1 is a flow sheet illustrating the solubilization and recovery of protective antigenic factors from parasite starting material according to the process of the present invention.

In a general embodiment, as shown in FIG. 1, the parasite material is suspended to the desired concentration in a suitable diluent, such as distilled water or an aqueous isotonic saline solution, and the non-ionic detergent added with agitation to solubilize the insoluble antigenic factors and form a dispersion system having a dispersed phase including the solubilized parasite antigenic factors and the detergent, and an undispersed phase including insoluble parasite material components. The dispersed phase is separated from the undispersed phase, conveniently by centrifugation, and the solubilized antigenic factors are separated from the detergent, for example, by ultrafiltration, dialysis, gel filtration, freeze/thawing, or other conventional techniques. The reaggregated solubilized antigenic factors are then recovered from the dispersion medium, as by centrifugation. Typically, the dispersed phase will also include dispersed foreign material comprising some dispersed parasite components, as well as dispersed tissue or cell components if infected cells or tissues are employed as starting parasite material. While the dispersed foreign material remaining after detergent separation generally does not interfere with the efficacy of recovered antigenic factors in vaccines or as diagnostic agents, if desired, the antigenic factors may be further purified, for example in the presence of the dispersing agent by known techniques such as appropriate gel filtration procedures, salting out, immunoprecipitation or immunoadsorption using specific antisera or monoclonal antibody preparations, phase separation, or rate zonal or related separation techniques. It may also be desirable to add a protease inhibitor to suspensions of intact cells or tissues prior to rupturing to prevent the possible enzymatic destruction of immunoprotective proteins.

The compositions employed as diluents for suspending the starting parasite material and in the filtration procedures are aqueous diluent solutions compatible with the material to be diluted. Distilled water or isotonic salt solutions such as sodium chloride or phosphate buffer are particularly suitable. The pH of the suspension may vary considerably within an exemplary range of pH 4 to about pH 8 or 9; it is preferable, however, to maintain the biological material at a pH of about neutral to avoid the possibility of inactivating the desired antigenic factors. Electrolyte salts such as sodium chloride and calcium chloride may be added to the suspending medium so as to result in concentrations sufficient to bring about optimum solubilization effects in the presence of added detergent. The same is true for the addition of nonelectrolytes such as n-Octyl alcohol and n-Amyl alcohol. In still other instances chelating agents such as Ethylenediaminetetraacetic acid (EDTA) may be added to the suspending diluent to facilitate detergent solubilization of specific substances.

The concentration of the parasite starting material in the suspending diluent depends on the nature of the material. Partially isolated parasite starting material is appropriately suspended in concentrations of from about 0.5 to about 5 mg of protein per milliliter, depending upon the state of purification of the starting material; intact cells and tissues are generally suspended in diluent to a concentration of from about 1% to about 50% and most preferably 15% to about 30%.

Dispersing agent is added to the suspension of parasite material to give a concentration of from about 0.002M to about 0.4M, depending upon the characteristics of the detergent and the suspended material, as well as the concentration of the suspended material. Detergent is added to the starting parasite material preferably in an amount sufficient to obtain optimum activity of the recovered antigenic material; that is, in an amount which maximizes the immunoprotective material solubilized while retaining maximum biologic activity, and which minimizes the foreign material solubilized. Generally, detergents of a high extractive efficiency are preferred, especially such detergents which have little or no tendency to inactivate the protective antigenic factors to be recovered. Suitable dispersing agents are non-ionic detergents such as:

1. Polyoxyethylene propylene glycol monostearate (ATLAS G-2164); polyoxyethylene lauryl ether (BRIJ 35); polyoxyethylene sorbitan monolaurate, -palmitate, -stearate and, -oleate respectively (TWEEN 20,40,60 and 80 respectively) and polyoxyethylated tert-octylphenol (TRITON X-100).
2. Sorbitan monostearate, mono-oleate and -trioleate respectively (SPAN 60,80 and 85 respectively).
3. Nonylphenol polyoxyethylene ether (TERGITOL NPX).
4. Alkyl phenyl ethoxylate (NONIDET P40).

A particularly suitable dispersing agent, especially for blood-stage plasmodial antigenic factors, is

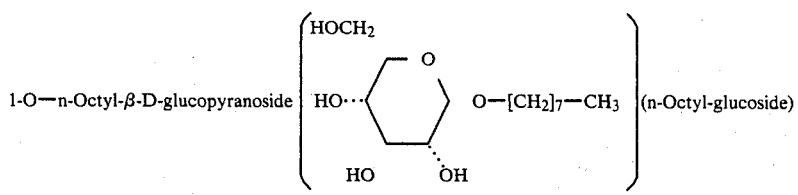

1-O—n-Octyl-β-D-glucopyranoside (n-Octyl-glucoside)

available from Boehringer Mannheim Biochemicals, Indianapolis, Ind. Other glucoside may also be used alone or in various combinations.

As set forth in the flow sheet of FIG. 1, after addition of the dispersing agent to the suspension of parasitic starting material, the suspension is preferably incubated for a period of time at temperatures which ensure substantial dispersion of the parasite antigenic factors while minimizing bacterial growth and avoiding inactivation of these factors. Typically, the dispersing agent is added to the suspension with agitation, and the admixture incubated for from a few minutes to up to 24 hours or more at temperatures ranging from about 3° C. to about 100° C., for example 4° C. to 37° C. The dispersed phase is then separated from the undispersed phase, conveniently by centrifugation at 250,000 g maximum at temperatures ranging from about 3° C. to about 37° C. until the unsolubilized material has aggregated or settled out, usually for about 15 minutes to 1 hour; the number of minutes actually employed will depend primarily upon the density of the suspension. Generally, a pellet of unsolubilized material is obtained, which may be further extracted. The supernatant dispersed phase is then subjected to gel filtration or other separation techniques to remove the detergent and further isolate the solubilized antigenic factors. After the detergent has been removed, the solublized antigenic factors reaggregate and are separated from the fraction, as by centrifuging at 250,000 g maximum for about 15 minutes to about 1 hour at from about 3° C. to about 10° C. Typically, the resultant reaggregation comprises pelletized material, which is then homogenized in a suitable isotonic diluent such as isotonic saline to a final protein concentration of from about 16 μg/ml to about 200 μg/ml, preferably from about 33 μg/ml to about 170 μg/ml, for use as vaccine. While it is not certain that the protective antigenic factors are proteins, there is a direct correlation between protein content and immunoprotective activity of the recovered material as determined be in vivo assays. If desired, the solubilized antigenic factors may be further purified prior to or after separation of the dispersing agent by known techniques described supra.

Figure 2A:
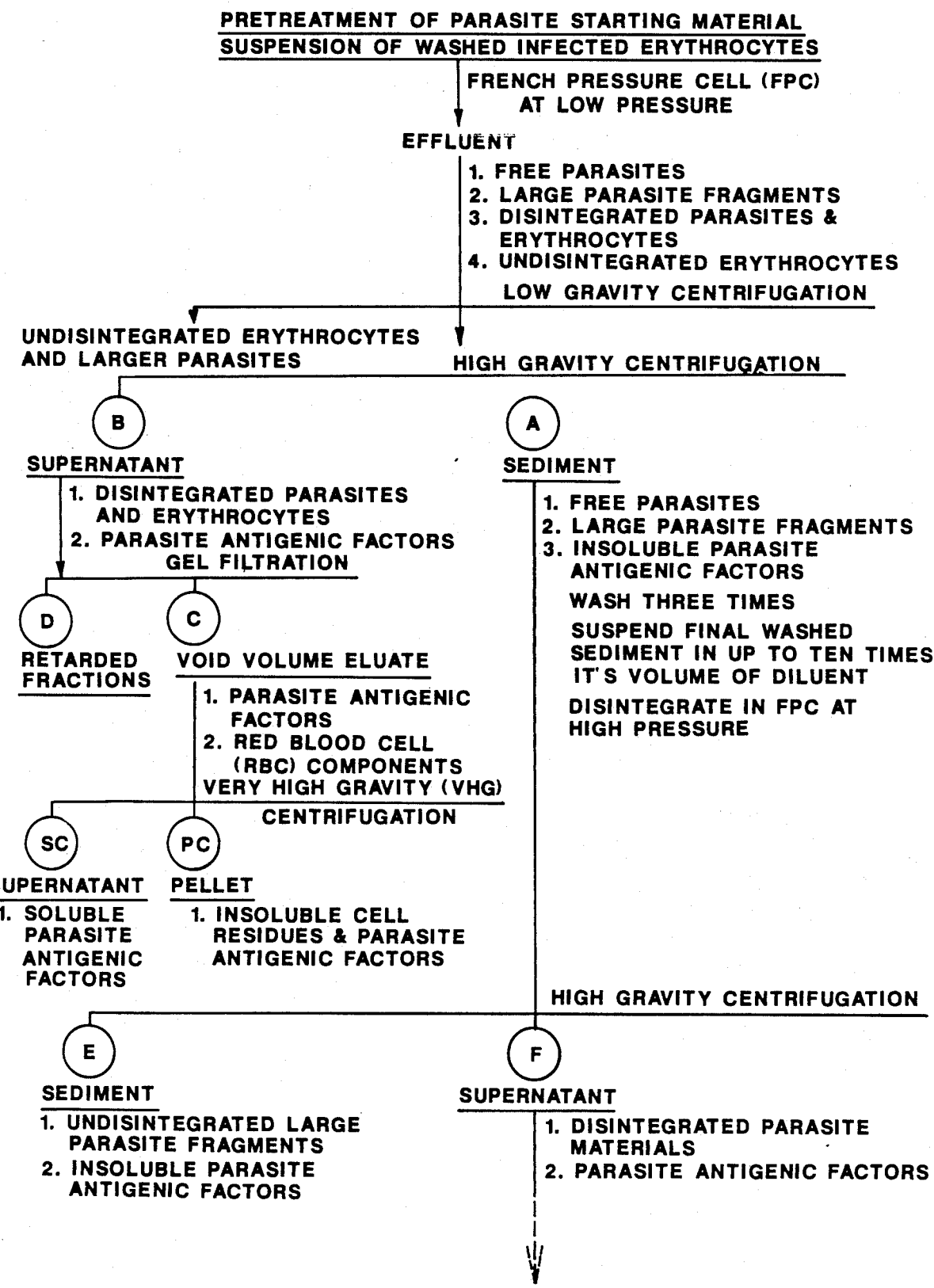
FIGS. 2A and 2B depict a flow sheet illustrating the pretreatment of parasite starting material to partially isolate parasite starting material components and associated protective antigenic factors.
Figure 2B:
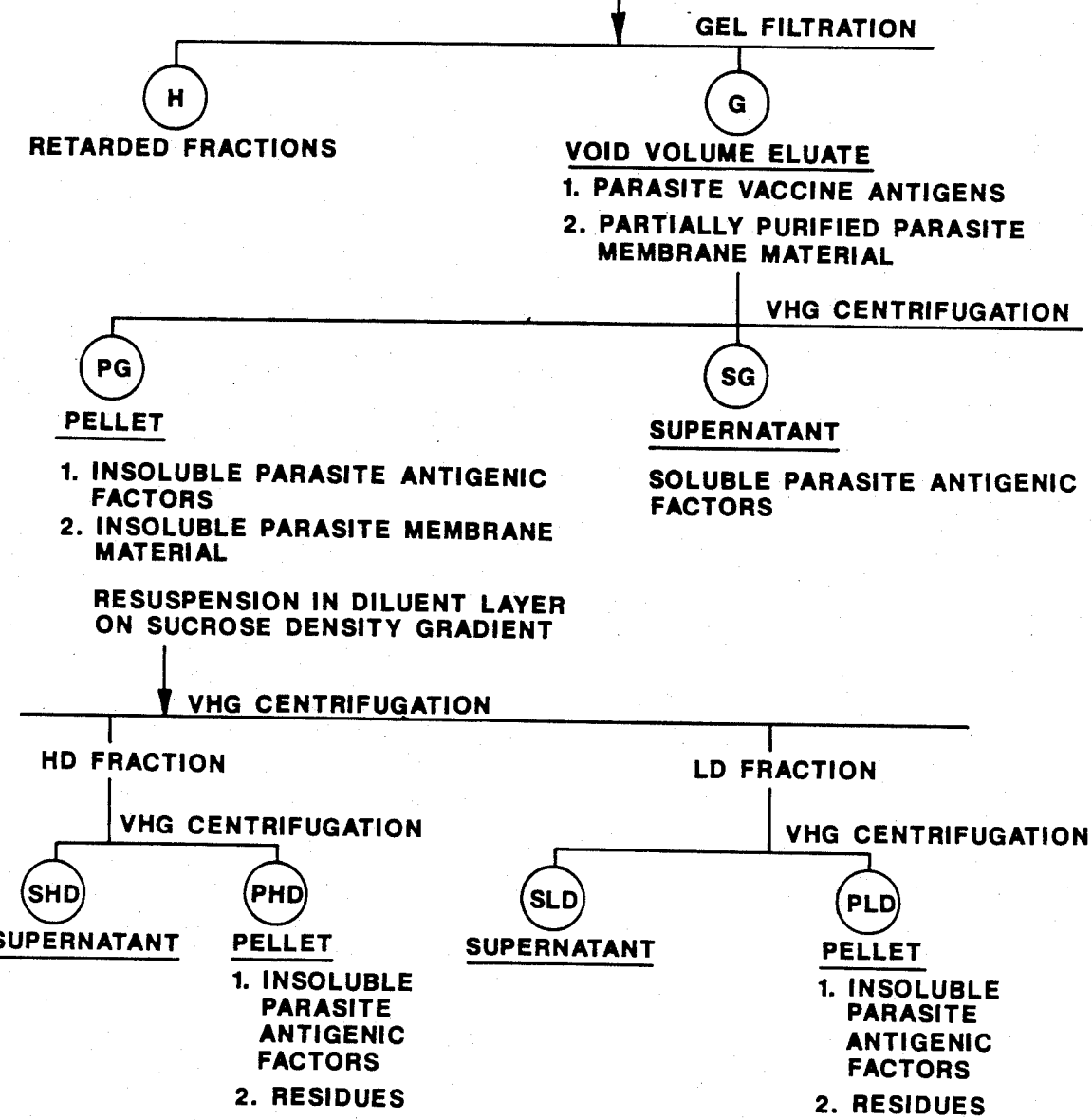

While it has been found to be generally preferable in terms of yield and process time to employ intact cells and tissues as the starting parasite material, particularly for blood-stage Plasmodium species, the pretreatment of intact cells and tissues to partially isolate insoluble plasmodial material prior to dispersion is contemplated. As set forth in the flow sheet of FIG. 2, the pretreatment of intact cells and tissues broadly comprises the selective disintegration of host cells or tissues while largely preserving the mechanically less fragile parasites, for example, by the use of French Pressure Cells, nitrogen cavitation methods as exemplified by the Parr bomb, the Riby or Hughes press, or ultrasonic techniques. The disintegrated tissue or cellular material is separated from the resulting free parasites or fragments in a series of fractionation and separation steps, and the fraction containing the parasite antigenic factors recovered, usually as isolated partially purified insoluble parasite components, typically membrane material in association with the parasite antigenic factors. This resultant isolated insoluble parasite material in association with parasite antigenic factors is employed as pretreated parasite starting material in the solubilization and recovery process of the invention. In FIG. 2, low pressure refers to FPC pressures between 800 and 2500 p.s.i. and high pressure to those between 3000 an 40,000 p.s.i. Low gravity refers to centrifugation forces between 50 and 1100 g maximum and high gravity to those between 7000 and 12,000 g maximum. VHG (very high gravity) refers to centrifugation forces of 200,000 g maximum more or less to 250,000 g maximum more or less.

The recovered parasite antigenic factors are useful in conferring immunity to infection by specific parasites in mammals and other vertebrates. The dosage ranges will vary, generally depending upon the animal to be immunized, the immunoprotective activity of the recovered antigenic factor fraction, and the specific parasite involved.

Since the immunoprotective antigenic factors have not been purified or identified and reliable in vitro tests for the presence of the antigens are not known to be available, it is very preferable, particularly in the case of vaccine to be administered to humans, that in vivo bioassays such as dose-response studies be performed on the actual material recovered according to the solubilization and recovery procedure of the present invention to determine the efficacy and toxicity of the recovered material. Such dose-response studies are well-known, and comprise an evaluation of the immunoprotective activity of the recovered material in an appropriate animal model system, typically rat, mouse or monkey model systems. An exemplary dose response study is set forth in Table 1, Sections II and III, wherein varying amounts of recovered solubilized parasite material, as measured by protein content, were administered to a group of mice subsequently challenged with the parasite. The administered material was statistically nontoxic at these dosage levels, and was efficacious at all dosage levels except the low dose PSR pellet material. Generally, for immunoprotective antigenic material recovered according to the process of the present invention, effective non-toxic dosage levels typically range from about 33 μg to about 170 μg of protein for a single-shot regimen; the range set forth is intended merely as a guideline however, and dosage levels outside this range may be found to be more satisfactory in some instances. Further, in determining optimum dosage levels, it is important to consider the well-known phenomenon that a non-immunizing dose of the antigenic material may be at a too high dosage level as well as a too low dosage level. Generally, the vaccine is administered by an usual route, parenterally or orally; the vaccine is conveniently administered i.p. in experimental animals, whereas i.v., subcutaneous, or intramuscular routes are preferred for reasons of safety in humans and non-experimental animals. Conventional carriers are employed with the recovered antigenic material for use as a vaccine, such as biocompatible isotonic salt solutions.

TABLE 2

COURSE OF INFECTION IN GROUPS OF A/J MICE TREATED AS INDICATED AND THEN CHALLENGED EIGHT OR MORE WEEKS LATER WITH *PLASMODIUM BERGHEI*, NK65D

| | | | Third Week Post Challenge | |
|---|---|---|---|---|
| Plasmodial Preparation | Protein Injected Per Mouse (μg) | No. of Mice[1] | Percent of Mice Surviving | Percent of Mice with 0%-1% Parasitemia |
| I Sucrose density gradient centrifugation fractions | | | | |
| A. Light density pellet fraction (PLD) | 15 | 5 | 100 | 100 |
| B. High density pellet fraction (PHD) | 79 | 5 | 100 | 60 |
| II Solubilized-recovered preparations | | | | |
| A. Pellet PSE from isolated parasite material | 33 | 5 | 100 | 100 |
| B. Pellet PSR from intact plamodially infected erythrocytes | | | | |
| a. High dose | 172–208 | 10 | 100 | 100 |
| b. Intermediate dose | 43–104 | 16 | 94 | 63 |
| c. Low dose | 13–26 | 12 | 92 | 9 |
| III Non-treated control mice | 0 | 29 | 79 | 0* |

[1]Does not include two mice from Group IIB and two mice from Group III which died within 24 hours of infection challenge. Postmortum examination of such animals revealed hemorrhaging in the peritoneal needle puncture site indicating inadvertent blood vessel damage.
*Parasitemia range 13%–57% (means 32% ± SD 12). In a combined study involving 98 non-treated control mice, 91 mice were still alive at three weeks post challenge with parasitemias ranging from 16% to 69% (mean 39% ± SD 10).

Once isolated, the vaccine material may be stored for future use by freezing or lyophilization. The unsolubilized material remaining from the starting preparation following the initial solubilizing step may be reextracted by reapplication of the described procedure or appropriate variations thereof.

Isolated antigenic material may also be employed for use in various in vivo and in vitro diagnostic tests. Such tests are useful in the detection, evaluation and following of infections with the related microorganism and for determining immunosensitivity to the involved antigen. The procedures for such tests are well known to those practiced in the discipline. The skin test is an example of an in vivo test. In this test antigen is administered by rubbing into scarified skin; intraderminal injection; or by application of a patch of material containing the antigen. The skin is then observed at the appropriate time afterwards for reaction indicative of sensitivity to the antigen. An example of an in vitro test is the direct slide agglutination test in which the serum to be tested is added to a suspension or emulsion of aggregated antigen on a glass slide and observed for a clumping of material. Similar type agglutination tests may be carried out using particulate objects such as erythrocytes, latex or polystyrene spherules or bentonite to which the antigens are first attached or adsorbed. Precipitation in fluid media or in gels are examples of other type tests. In such tests antisera is added to a solution or gel containing the antigen in soluble form and then observing for a precipitation reaction. Examples of fluid precipitation and gel precipitation tests are the interfacial ring test and the Ouchterlony immunodiffusion test respectively. Still other tests using the antigen in appropriate form (i.e. soluble or aggregated) are the complement fixation test and various antigen or antibody binding tests such as radioimmunoassay (RIA), enzyme linked immunosorbent assay (ELISA) and fluorescent antibody (FA) tests.

An exemplary in vitro test for cellular sensitivity is the lymphocyte transformation test in which antigenic factors are added to a culture of lymphocytes and the culture than assessed at the appropriate times for the level of induced lymphocyte transformation. Where appropriate, the antigenic factors in solution with detergent present may be used in test procedures requiring the antigenic factors in soluble form. An elaboration of the above described procedures can be found in *Manual of Clinical Immunology*, N. R. Rose and H. Friedman, Eds. (The American Society for Microbiology, 1976); Barrett, J. T. *Basic Immunology and its Medical Application* (The C. V. Mosby Co., 1980) P. 128; and in *Immunological and Serological Aspects of Clinical Parasitology*, W. Ball and V. Iralou, Eds. (Eastern Penn. Branch of the Am. Soc. for Microbiology. P. 1, P. 15 and P. 27, 1981).

The following Examples illustrate the practice of the present invention.

EXAMPLE I

ISOLATION AND PARTIAL PURIFICATION OF BLOODSTAGE PLASMODIAL MATERIAL FROM HOST RED BLOOD CELLS (PRETREATMENT OF PARASITE STARTING MATERIAL)

A. Isolation from Host Red Blood Cells as Shown in FIG. 2

Blood infected with the desired specie of malaria is collected in an anticoagulant solution such as heparin or Alsever's solution. The red cells are separated from the plasma by centrifugation in the cold (4° C.) at 3500 g for at least five minutes. The plasma and buffy coat is removed by aspiration and the cells are resuspended in a diluent comprising isotonic (0.15M) sodium chloride and recentrifuged. Three additional washings are employed with the aspiration of any remaining buffy coat each time to assure removal of the white blood cells.

The washed cells are resuspended in a volume of NaCl diluent sufficient to give a 20% suspension and then placed in a cooled (4° C.) French Pressure Cell. The suspended blood is slowly passed through the needle valve of the French Pressure Cell at a pressure of about 800 p.s.i. The pressure used for this step depends on the predetermined optimum pressures for the particular specie of Plasmodium, host red cell, and stage of the parasite; the pressure advantageously is from about 800 p.s.i. to about 2500 p.s.i. The first 2-3 ml of effluent are discarded to avoid contamination with the few unruptured erythrocytes which may initially pass through the needle valve.

The above procedure selectively disintegrates the host red cells while largely preserving the mechanically less fragile malaria parasite. While nearly all of the red cells, both infected and non-infected, present in the malarious blood are finely disintegrated, a large number of free intact parasites and large parasite fragments remain. Any intact red cells escaping disintegration may be separated from the French Pressure Cell effluent by centrifugation at between 50 g and 1100 g maximum for ten minutes.

The supernatant contains the free parasites, large parasite fragments and a mixture of disintegrated erythrocytes and whatever parasites are disintegrated. The free parasites and large parasite fragments are separated from the disintegrated materials by centrifugating at from about 7000 g to about 12,000 g maximum for up to 30 minutes at temperatures facilitating separation, for example about 3° C. to about 10° C.

The parasite sediment resulting from the above centrifugation contains the free parasites and larger parasite fragments and is almost completely free of the original host red cell stroma. The sediment A is washed three times by resuspension and centrifugation (7000 g to 12,000 g maximum), and finally resuspended in a volume of diluent 8 times the volume of parasite sediment as estimated to give the final desired concentration of parasite vaccine fraction. A volume of diluent 7 to 10 times the volume of parasite sediment will generally result in a final vaccine fraction near that needed for vaccination procedures.

The resuspended washed parasite material is passed through the French Pressure Cell at a pressure of 20,000 p.s.i. Pressures from about 300 p.s.i. to 40,000 p.s.i. are suitable. Following the high pressure passage, i.e., 3000 to 40,000 p.s.i., the effluent is centrifuged from about 7000 g to about 12,000 g maximum for 30 minutes at 4° C. to remove any undisintegrated parasite material E. The resulting supernatant F contains the disintegrated parasite components not sedimented at the gravity force and time employed. The supernatant F contains the parasite vaccine antigen factors along with a relatively large amount of parasite iron-containing pigment (hemazoin) and other parasite components.

Further isolation of the parasite antigenic factors is accomplished by gel filtration with Bio-Gel employing the isotonic saline diluent as eluant. Molecular sieve materials such as various Sephadex (i.e., Sephadex G-200), Sepharose and Bio-Gels may be used. The material appearing in the void volume eluate contains isolated partially purified parasite membrane material in association with the malaria vaccine antigenic factors. Fraction G is substantially serologically free of host stromal contamination and acts as a specific complement fixing antigen in the serological detection and diagnosis of malaria. *Plasmodium berghei* and *Plasmodium knowlesi* derived preparations of G were used to vaccinate mice and monkeys, respectively, against the homologous malaria. Fraction G contains a relatively large amount of hemazoin, which though it does not interfere with the fraction's vaccine or serologic properties, must be taken into account when attempting to relate the fraction's protein content to its vaccine concentration.

B. Subfractionation of the Isolated Membrane Material

Centrifugation of eluate G at 250,000 g maximum for 30 minutes at 40° C. results in the production of a colorless supernatant (SG) and a brownish firm pellet (PG).

Isolated plasmodial products A, B, C, E, F, PC, G and PG are immunoprotective and contain membrane material. For instance, on ultrastructural analysis (see Reference VI), Product E was found to consist of membranous structures interspersed with "cellular debris" and product PG was found to consist of large numbers of membranous strands and vesicles interspersed with what appeared to be membrane bound pigment material (hemazoin).

Host cell contamination of either pellet PG or the void volume eluate G from which it is derived was absent.

PG is further fractionated by sucrose density gradient centrifugation (see Reference VI). This is accomplished by resuspension of PG by homogenization into diluent with a teflon-glass homogenizer to a concentration of approximately 0.7 mg of protein per milliliter, layering on a 20% to 50% preformed linear sucrose density gradient, and centrifuging at 217,500 g maximum for two hours at 4° C. Two zones of turbidity develop within the gradient, which upon fractionation, resolves into 260/280 nm absorption peaks in the 20%-22% and 26%-35% sucrose zones respectively. These are respectively designated as the light density (LD) and heavy density (HD) peaks. Dilution and cdentrifugation of each of these fractions at 250,000 g maximum for 60 minutes at 4° C. results in the formation of an LD and HD pellet. On ultrastructural analysis (see Reference VI), both pellet LD and HD are found to consist of membrane strands and vesicles with an occasional dense strand reminiscent of two closely applied unit membranes. Parasite pigment material is also occasionally seen.

The LD and HD membranous pellets have been found to protect mice against the homologous malaria infection (see Reference VI). Preparation LD appears to be significantly more potent than HD. For instance, in one experiment, groups of A/J mice were injected one time intraperitoneally (ip) with 16 $\mu$g of LD or 79 $\mu$g of HD protein respectively. Eleven and one-half weeks later, the mice were challenged ip with $10^7$ *P. berghei* NK65D homologously infected mouse red blood cells. At three weeks post challenge, all of the mice injected with LD had 0%-1% parasitemias. Only 60% of those receiving HD had corresponding parasitemias in the same time period. Non-treated A/J mice, as described below, respond to such infection challenge with parasitemias at the end of three weeks ranging from approximately 13% to 69% or higher.

The above results affirm the association of the plasmodial protective antigenic factor with the parasite membrane and indicate that preparation LD is a good point of departure for the identification and further purification of such antigenic factors.

Some of the parasite protective antigenic factors occur in soluble form (see Reference VI). Thus, when fraction F is chromatographed through Bio-Gel A-150 m (fractionation range $10^6$ to $150\times10^6$D) (Bio-Rad Laboratories, Richmond, Calif.), two major 260/280 nm absorption peaks are produced. They are a turbid void volume peak containing fraction G and a clear colorless final peak near termination of the fractionation run. Fifty percent of A/J mice injected one time ip with second peak material were protected against subsequent parasite challenge. In addition, variable protection was imparted by the supernatant (SG) remaining following removal of the membranous particulate material from the Bio-Gel A-150 m void volume peak. It appears that the soluble protective material is in some way associated with the membrane material and is separated from it by the conditions of preparation. The procedures of Example I are elaborated in References IV, VI,II,III and U.S. Pat. No. 3,849,551, all incorporated herein by reference.

EXAMPLE II

SOLUBILIZATION AND RECOVERY OF THE PLASMODIAL PROTECTIVE ANTIGENIC FACTORS

In the procedures to be described, mouse red blood cells infected with *P. berghei* NK65D were used as the source of infective and vaccine material. Isotonic saline was used as diluent throughout and all gel filtrations were carried out at ambient temperatures. Protein determinations were carried out by the method of Lowry (Lowry, et al., *J. Biol. Chem.*, 193:265–275, 1951) as modified by Yu, et al., *Anal. Biochem.*, 24:523–530, 1968, except where indicated.

A. Background

Example I describes steps for the pretreatment of parasitic starting material retaining antigenic factors still in association with the insoluble parasite components and, in particular, with the parasite membrane. Although a small quantity of vaccine material appears to separate in soluble form from the parasite during processing, the quantity of material so recovered is small and its potency variable. Example II describes a systematic procedure for effectively separating large quantities of the insoluble parasite antigenic factors in soluble form which permits final purification and characterization of such antigenic factors and offers a practical means for the production of an antimalarial vaccine and related diagnostic agents. Highly active malaria antigenic factors were effectively solubilized from isolated insoluble plasmodial material (IIB) and intact plasmodially infected RBC (IIC).

The A/J mouse model malaria vaccination system (see Reference I) was used for the detection and comparative immunogenic evaluation of solubilized recovered plasmodia antigen(s). CF-1 mice served as a source of infected and non-infected blood. The reticulocyteinfecting *Plasmodium berghei* strain NK65 (Line D), obtained from the University of Illinois, Urbana, Ill., served as a source of plasmodial protective and infective material.

The non-ionic dispersing agents employed are generally compatible with biochemical and immunochemical separation procedures. The non-ionic detergent n-Octylglucoside used in this exemplary process is an excellent example of such dispersing agents. In this process highly active malaria antigenic factors were effectively solubilized from isolated insoluble plasmodial material (B) and intact plasmodially infected red blood cells (C).

B. Solubilization and Recovery of Malaria Vaccine Antigenic Factors from Isolated Insoluble Plasmodial Material, as Shown in FIG. 1

Isolated *P. berghei* NK65D plasmodial material represented by fraction E of Example I was homogenized in isotonic saline diluent with a teflon-glass homogenizer to a concentration of 1.2 mg of protein per milliliter. The suspension was placed in a beaker and rapidly stirred with a magnetic bar stirrer while n-Octylglucoside powder was slowly added to the final concentration of 0.03M (6.75 mg detergent per mg protein present). The mixture was incubated at 4° C. for four hours and then centrifuged at 250,000 g maximum for 30 minutes at 4° C. to remove unsolubilized material. The resulting pellet was set aside for repeated extractions and the clear supernatant eluted with isotonic saline diluent through Bio-Gel P-100 at ambient temperatures in order to remove the dispersing agent and further isolate the vaccine-containing fraction. Removal of the dispersing agent resulted in the production of a turbid void volume eluate. The 260/280 nm absorption of each void volume fraction was determined, the fractions combined, and the 260/280 nm absorption determined for the combined pool. The combined pool was centrifuged at 260,000 g maximum for 30 minutes at 4° C. and the obtained translucent yellow-brown pellet (PSE) surface washed and homogenized into isotonic saline to a final protein concentration of 33 µg per milliliter. The clear colorless supernatant was discarded. The resuspended pellet was evaluated for vaccine activity as described below.

C. Solubilization and Recovery of Malaria Vaccine Material from Intact Plasmodially Infected Red Blood Cells, as Shown in FIG. 1

While the procedure described in "B" above utilized a starting preparation which is highly homogenous with respect to parasite material and is necessary as a means of establishing the relationship of the solubilized protective antigenic factors to the insoluble parasite components, pretreatment is lengthy, complex and produces a low yield of vaccine material relative to the quantity of starting infected blood. It is desirable to directly disperse the protective antigenic factors from the starting intact infected blood and thereby simplify the procedure, reduce its length and maximize the recovery of vaccine material, which might otherwise be lost during preparation of the isolated parasite material (such as membrane associated antigens and antigens which might be associated with the red cell or the parasite cytoplasmic phase).

Washed mouse red blood cells which were 19% infected with malaria parasites were suspended to 20% in isotonic saline containing 0.03M n-Octylglycoside (44 mgm of glucoside per milliliter of packed red cell equivalent) and incubated overnight at 4° C. Following incubation, the unsolubilized material was removed by centrifugation at 250,000 g maximum at 4° C. for 60 minutes to insure complete removal of unsolubilized material from the relatively dense hemaglobin containing suspension. The obtained pellet was set aside for repeated extractions and the clear supernatant subjected to gel filtration for separation of the antigen containing fraction from the solubilizing agent, various other parasite substances, and the accompanying hemaglobin and dispersed red cell constituents. In order to handle the large volumes of supernatant involved and to insure sufficient gel capacity to remove the high concentration of hemaglobin present, gel filtration was carried out in a large 5 cm by 50 cm glass column filled with Bio-Gel A-1.5 m. Up to 25 milliliters of supernatant could be effectively fractionated at one time in this way. All fractionations were carried out at ambient temperatures. The obtained turbid void volume eluate was spectrophotometrically measured, combined and centrifuged as before. The supernatent was discarded and the obtained translucent yellow-brown pellet PSR resuspended in saline by homogenization. Various concentrations of the resuspended pellet PSR were then evaluated for protective immunogenicity as described below.

In a comparative study, non-infected mouse red cells which were similarly treated produced barely perceptible turbidity in the corresponding gel filtration void volume volume eluate which had a 260/280 nm absorption approximately one eighth that obtained for the corresponding infected red cell fractions. Similarly, the pellet obtained following centrifugation of the non-infected red cell derived void volume eluate was significantly smaller than that obtained from the infected cell preparation. The foregoing findings indicate that the vaccine containing parasite pellet material (PSR) is selectively and preferentially separated from the host red cell components.

EXAMPLE III

EVALUATION OF THE VACCINE ACTIVITY OF THE SOLUBILIZED RECOVERED PLASMODIAL FRACTIONS PSE AND PSR

Respective groups of A/J mice were injected one time ip with one milliliter of preparation PSE or respective concentrations of PSR as shown in Table 1. Eight to eleven weeks later, the treated mice along with non-treated control mice were challenged ip with $10^7$ plasmodially infected mouse red blood cells and parasitemia levels for each mouse determined weekly. Successfully vaccinated mice responded with low level parasitemias which began to resolve by the second and third weeks post challenge. Non-treated mice, on the other hand, experienced progressively increasing parasitemias, which did not begin to resolve, in those destined to survive, before the fifth week post challenge.

As can be seen in Table 1, all of the mice receiving PSE (Group II-A) were still alive at the end of three weeks post challenge and all were without detectable parasitemias. The pattern of survival and parasitemia by the third week post challenge for the groups of mice receiving various concentrations of PSR were dose related. Thus, at three weeks post challenge (Table 10, 100% of mice receiving 172 $\mu$g to 208 $\mu$g of preparation PSR protein were still alive. Ninety-four percent of those receiving 43 $\mu$g to 104 $\mu$g and 92% of those receiving 13 $\mu$g to 26 $\mu$g of preparation PSR protein, respectively, were still alive at the end of the same time period. The percentage of mice in each group with third week parasitemias of less than 1% were 100%, 63% and 9%, respectively, for those receiving the high, intermediate or low dose respectively.

At the end of three weeks post challenge, 79% of the non-treated control mice were still alive. Parasitemia levels in these animals ranged from 13% to 57% (mean 32%±SD12). Similarly, in a study combining the results of infection in A/J mice with P. berghei NK65D, ninety-one out of a starting total of ninety-eight were still alive at three weeks post challenge. Third week parasitemia levels in these animals ranged from 16% to 69% (means 39%±SD10).

The above results clearly establish the vaccine character of the solubilized recovered plasmodial fractions PSE and PSR and demonstrate that the level of protection attained is dose related. In addition, the higher level of potency seen per unit of protein present in preparation PSE indicates that the plasmodial material first separated from the host red cell yields a solublized recovered product which is significantly enriched with respect to the vaccine antigenic factors. This is in conformity with the increased potency observed with the highly purified membrane subfraction LD described supra, and supports the theory that further purification of the solubilized vaccine antigenic factors (whether due to the vaccine antigen enrichment, or removal of interfering antigens and/or possible immunosuppressive substances) will result in still more potent effects. Such effects would be in contrast to the putative intrinsic "weakness" attributed to malaria vaccine antigenic factors based on the use of crude preparations in various animal studies in the past.

EXAMPLE IV

A vaccine was prepared by incubation of a 30% suspension of infected mouse red blood cells in a 0.07M n-Octylglucoside solution (70 mg of glucoside per packed cell equivalent) for 30 minutes at 4° C. The remainder of the vaccine recovery procedure was according to Example II (C) for processing intact infected blood. Four out of six A/J mice treated one time ip with an estimated* 200 $\mu$g of the obtained PSR material were protected against infection challenge at just 2½ weeks after treatment. The rapidly attained vaccination response (i.e., 2½ weeks as opposed to the usual 8 to 12 week waiting period) indicates that the vaccine material isolated as described is unusually potent and that the solubilization and recovery technique produces antiparasitic vaccine preparations with greatly enhanced activity.
*Estimated from 260/280 O.D.

The solubilization and recovery process of the present invention allows for recovery of antigenic factors which can function as vaccine or diagnostic agents or both. The procedures described, along with any number of variations, will allow for the practical separation and purification of specific antigens for the first time and opens the way for their use in a variety of immunological, immunobiological and immunodiagnostic ways.

Antiparastic vaccines developed by the procedures described may be individual vaccines for each specie of parasite to be protected against or a combination of various species to form polyvalent vaccines. The vaccines could, in addition, be composed of antigenic factors from different stages of the parasite so as to form a "multi" vaccine. Finally, blood stage malaria or other parasite vaccines could be made up of a combination of antigenic factors derived from different lots of parasites of the same specie in order to insure protection against heterologous strain variants, should they exist.

The various antigenic factors, once isolated, could also be biochemically altered so as to increase their immunization potency, should this prove necessary. Such alterations could range from intrinsic changes in the molecular structure of such antigenic factors to coupling them to powerful immunostimulating carrier molecules. The vaccine antigenic factors themselves may eventually be either partially or completely synthesized by biochemical or recombinant DNA techniques. As with the naturally derived antigenic factors, those produced by such synthetic techniques could also be separated from the "matrix" with which they may be associated by appropriate application of the procedures described.

What is claimed is:

1. A method for the solubilization and recovery of plasmodial parasite protective antigenic factors from associated starting plasmodial parasite material, starting material being selected from the group consisting of intact red blood cells containing the blood stage of the plasmodial parasite, intact plasmodial parasite cells or fragments of such cells released from red blood cells, merozoites which have released themselves from red blood cells, tissues having blood infected with the plasmodial parasite tissues having blood infected with the plasmodial parasite, and tissues having plasmodial parasite infected blood, and method comprising:
   (a) forming an aqueous suspension of the starting parasite material and associated insoluble protective antigenic factors;
   (b) adding the non-ionic detergent n-octyl-β-D-glucopyranoside to the suspension to solubilize the insoluble antigenic factors; and
   (c) recovering the solublized plasmodial parasite protective antigenic factors.

2. A vaccine for conferring immunity to mammals or other vertibrates against infection by a plasmodial parasite comprising the protective antigenic factors of that parasite recovered from associated parasite starting material, said starting material being selected from the group consisting of intact red blood cells containing the blood stage of the plasmodial parasite, intact plasmodial parasites released from red blood cells, merozoites which released themselves from red blood cells, tissues having blood infected with the plasmodial parasite, and tissues having plasmodial parasite infected blood, the vaccine having been made by:
   (a) forming a suspension of the starting parasite material and associated insoluble protective antigenic factors in an aqueous medium;
   (b) adding the non-ionic detergent n-octyl-β-D-glucopyranoside to the suspension to solubilize the insoluble antigenic factors; and
   (c) separating and recovering the solublized protective antigenic factors from the aqueous medium.

3. A method for the purification and recovering of protective antigenic factors of plasmodial protozoan parasites from associated starting parasite material, said starting material being selected from the group consisting of intact red blood cells containing the blood stage of the plasmodial parasite, intact plasmodial parasites released from red blood cells, merozoites which released themselves from red blood cells, tissues having blood infected with the plasmodial parasite, and tissues having plasmodial parasite infected blood, said method comprising:
   (a) forming a suspension of the starting parasite material and associated protective antigenic factors in an aqueous suspension medium;
   (b) adding the non-ionic detergent n-octyl-β-D-glucopyranoside to the suspension to solubilize the insoluble antigenic factors and form a dispersion system having a dispersed phase including the solubilized parasite protective antigenic factors and the non-ionic detergent and an undispersed phase including protective insoluble parasite material;
   (c) separating the dispersed phase from the undispersed phase;
   (d) separating the detergent from the dispersed phase to aggregate the protective antigenic factors; and
   (e) recovering the aggregated antigenic factors from the suspension medium.

4. A method of conferring immunity against parasite infection upon a mammal or other vertebrate, said method comprising:
   (a) preparing a vaccine by the process of forming a suspension of starting parasite material and associated insoluble protective antigenic factors, said starting material being selected from the group consisting of intact red blood cells containing the blood stage of the plasmodial parasite, intact plasmodial parasites released from red blood cells, merozoites which released themselves from red blood cells, tissues having blood infected with the plasmodial parasite, and tissues having plasmodial parasite infected blood, in an aqueous medium;
   ii. adding the non-ionic detergent n-octyl-β-D-glucopyranoside to the suspension to solubilize the insoluble protective antigenic factors; and
   iii. separating and recovering the solubilized protective antigenic factors from the aqueous medium; and
   (b) parenterally administering the vaccine to the mammal or other vertibrate in one or more immunity-conferring doses.

5. A method for the solubilization and recovery of plasmodial parasite protective antigenic factors from associated starting plasmodial parasite material, said starting material being selected from the group consisting of intact red blood cells containing the blood stage of the plasmodial parasite, intact plasmodial parasite cells or fragments of such cells released from red blood cells, merozoites which have released themselves from red blood cells, tissues having blood infected with the plasmodial parasite, and tissues having plasmodial parasite infected blood, said method comprising:
   (a) forming a suspension of the starting parasite material and associated insoluble protective antigenic factors;
   (b) adding the non-ionic detergent n-octyl-β-D-glucopyranoside to the suspension to disperse the insoluble antigenic factors while preserving the protective capability of said factors;
   (c) removing said detergent to yield aggregated plasmodial antigenic protective factors; and
   (d) recovering the aggregated plasmodial parasite protective antigenic factors.

6. A vaccine for conferring immunity to mammals or other vertebrates against infection by a plasmodial parasite comprising the protective antigenic factors of that parasite recovered from associated parasite starting material, said starting material being selected from the group consisting of intact red blood cells containing the blood stage of the plasmodial parasite, intact plasmodial parasites released from red blood cells, merozoites which released themselves from red blood cells, tissues having blood infected with the plasmodial parasite, and tissues having plasmodial parasite infected blood, the vaccine having been made by:
   (a) forming a suspension of the starting parasite material and associated insoluble protective antigenic factors;
   (b) adding the non-ionic detergent n-octyl-β-D-glucopyranoside to the suspension to disperse the insoluble antigenic factors while preserving the protective capability of said factors;

(c) removing said detergent to yield aggregated plasmodial protective antigenic factors; and, (d) separating and recovering the aggregated protective antigenic factors.

7. A method of conferring immunity against parasite infection upon a mammal or other vertebrate, said method comprising:

(a) preparing a vaccine by the process of
i. forming a suspension of starting parasite material and associated insoluble protective antigenic factors, said starting material being selected from the group consisting of intact red blood cells containing the blood stage of the plasmodial parasite, intact plasmodial parasites released from red blood cells, merozoites which released themselves from red blood cells, tissues having blood infected with the plasmodial parasite, and tissues having plasmodial parasite infected blood;
ii. adding the non-ionic detergent n-octyl-B-D-glucopyranoside to the suspension to disperse the insoluble protective antigenic factors while preserving the protective capability of said factors;
iii. removing said detergent to yield aggregated plasmodial protective antigenic factors; and,
iv. separating and recovering the aggregated protective antigenic factors from the medium; and, b. parenterally administering the vaccine to the mammal or other vertebrate in one or more immunity-conferring doses.

8. The method of claims 1 or 5 wherein said starting material is pretreated to partially purify the starting parasite material and protective antigenic factors.

9. The method of claims 1 or 5, wherein the cells are erythrocytes infected with a parasite species of the genus Plasmodium.

10. The method of claims 1 or 5, wherein the parasite species causes malaria.

11. A vaccine comprising the antigenic factors recovered according to the process of claim 3.

12. The vaccine of claim 11, wherein the recovered aggregated antigenic factors are resuspended in an isotonic diluent to a protein concentration of from about 15 $\mu$g/ml to about 200 $\mu$g/ml.

13. The vaccine of claims 2, 11, 12 or 6, wherein the parasite is a species of the genus Plasmodium.

14. The vaccine of claim 2, wherein the starting parasite material comprises intact erythrocytes or other blood tissue infected with a parasite of the genus Plasmodium.

15. The invention of claim 1 wherein the step of recovering the solubilized plasmodial parasite protective antigenic factors comprises:
recovering a portion of the solubilized parasite material and leaving plasmodial protective antigenic factors remaining in said suspension with the detergent;
further purifying the factors remaining in said suspension; and
recovering said remaining plasmodial antigenic factors free of the detergent.

* * * * *